United States Patent [19]

Elliott et al.

[11] Patent Number: 4,902,226
[45] Date of Patent: Feb. 20, 1990

[54] DENTAL AIR SUPPLY SYSTEM

[76] Inventors: Raymond D. Elliott, 1569 S. Pearl St., Denver, Colo. 80210; Herbert G. Cooper, 922 S. Vrain St., Denver, Colo. 80219

[21] Appl. No.: 188,498
[22] Filed: Apr. 29, 1988
[51] Int. Cl.$^4$ ............................................. A61C 1/02
[52] U.S. Cl. .................................... 433/104; 417/372
[58] Field of Search ................... 433/104, 98, 101; 417/372

[56] References Cited

U.S. PATENT DOCUMENTS

| | | | |
|---|---|---|---|
| 2,606,430 | 8/1952 | Pownall | 62/117.6 |
| 3,945,216 | 3/1976 | Schibbye | 62/84 |
| 4,060,340 | 11/1977 | Yanik et al. | 417/28 |
| 4,091,638 | 5/1978 | Mitch | 62/470 |
| 4,311,439 | 1/1982 | Stofen | 417/313 |
| 4,359,085 | 11/1982 | Mueller | 433/104 |

Primary Examiner—John J. Wilson
Attorney, Agent, or Firm—James E. Pittenger Fields, Lewis, Pittenger & Rost

[57] ABSTRACT

A portable dental delivery system is provided which is composed of a plurality of individual module sections. The portable delivery system provides all basic tools and accessories which are necessary for a dentist to perform all types of dental work which may be required by patients. The dental delivery system includes a quiet running, pressurized clean air supply system for operating the various tools and accessories utilized by the dentist. A hermetically enclosed refrigeration compressor unit is modified to provide an adequate supply of pressurized air in an extremely quiet manner. The temperature of the compressor unit is maintained at a safe level by an oil cooling system. A pump draws oil from the base of the compressor unit, passes it through a radiator which is additionally cooled by an axial fan. The oil is returned to the compressor unit at the top of the housing at a location which will cause the oil to impinge directly upon the cylinder head of the compressor. Oil entrained in the pressurized outlet air is collected in an oil coalescer. A check valve is provided downstream of the coalescer and ahead of an air storage tank. A normally closed solenoid is connected to the lowermost portion of the coalescer so that upon deenergization of the compressor unit the solenoid is automatically opened unloading the outlet pressure so as to drive any accumulated oil in the coalescer back into the oil return line for the housing.

17 Claims, 3 Drawing Sheets

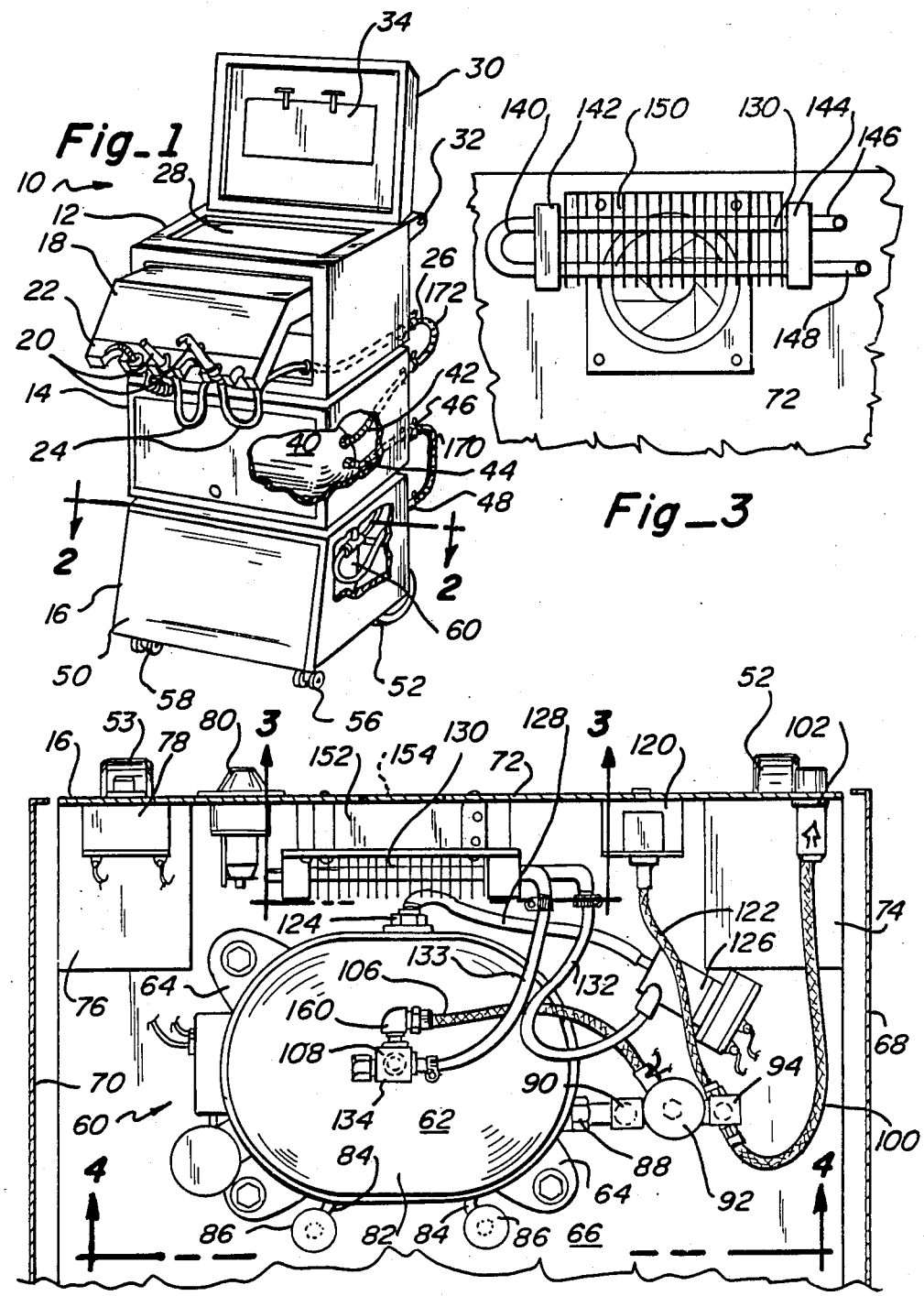

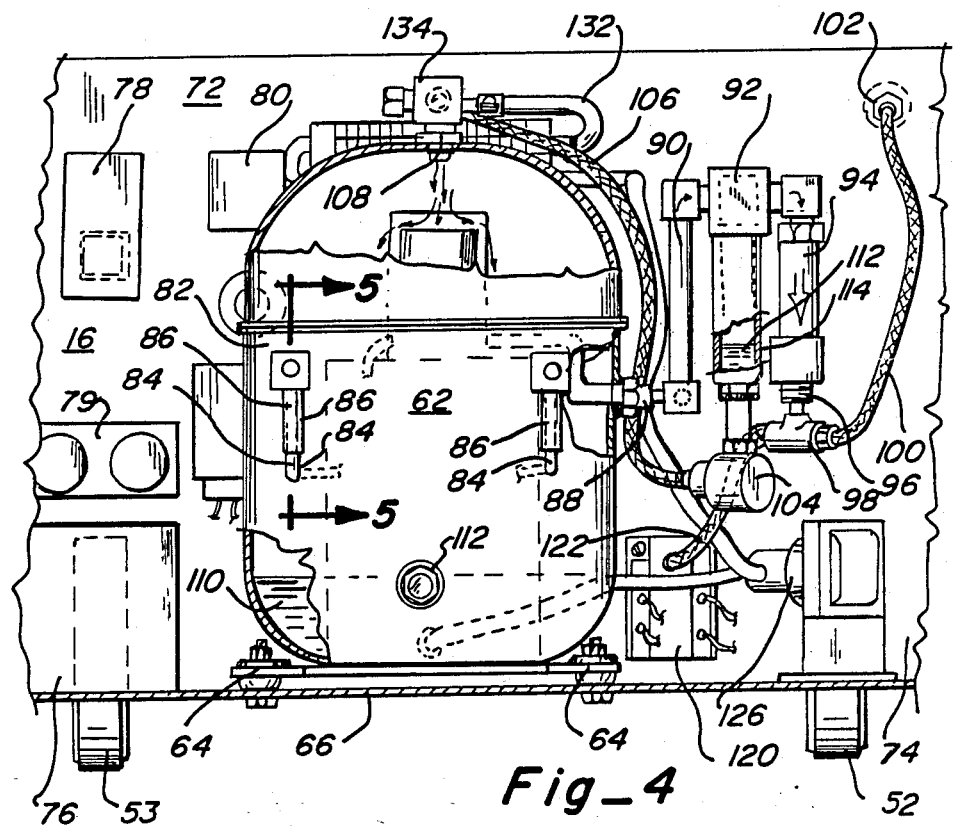
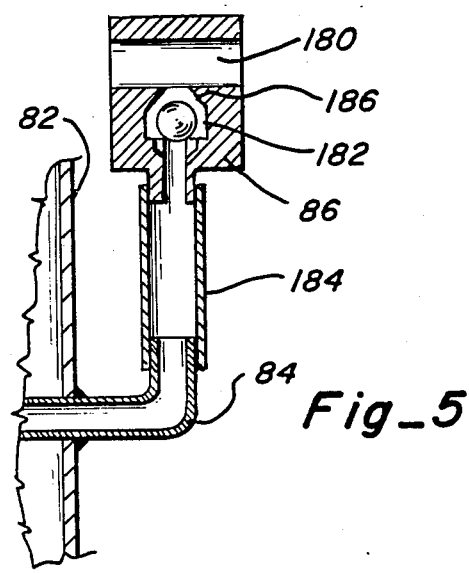
Fig_4
Fig_5

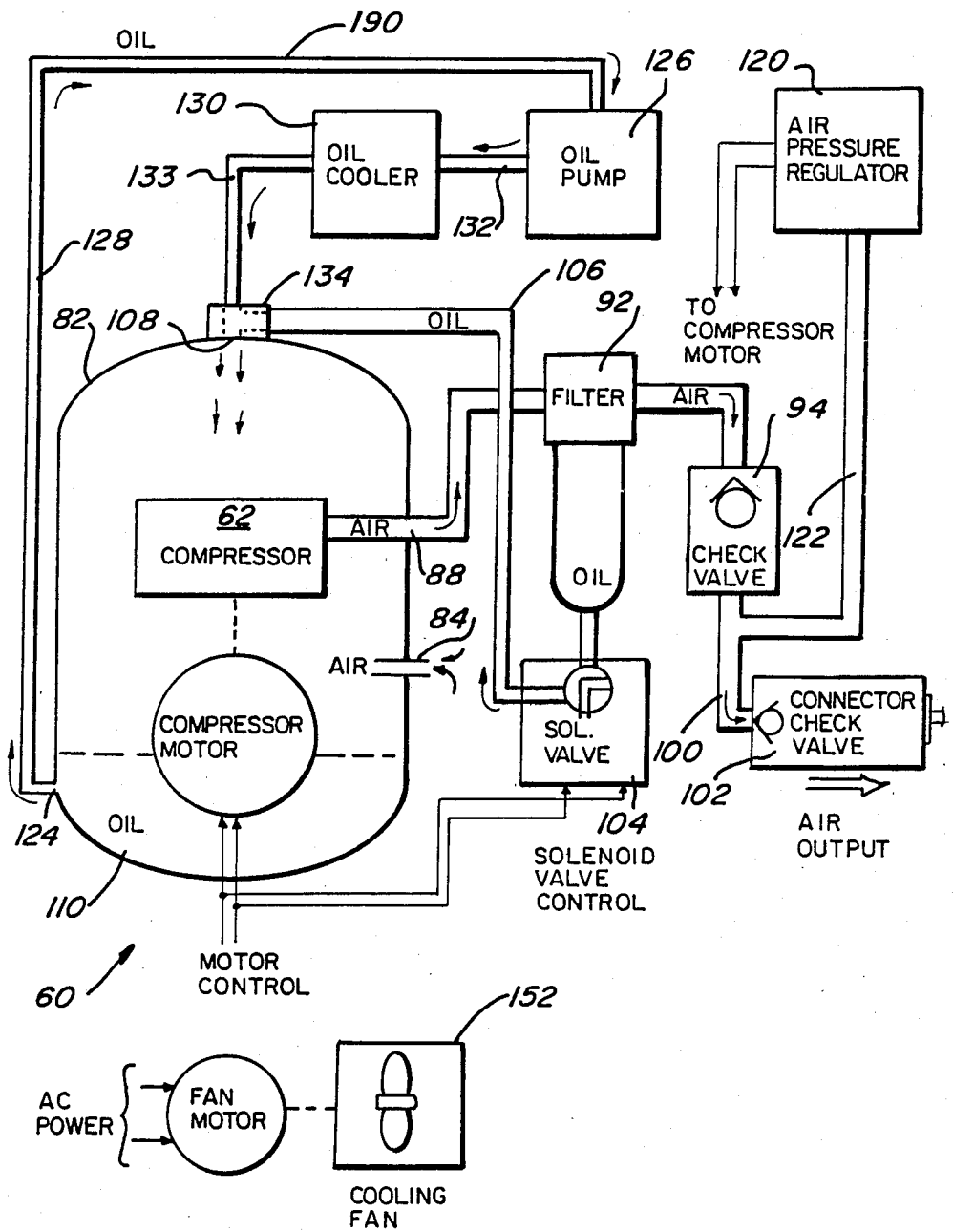
Fig_6

DENTAL AIR SUPPLY SYSTEM

FIELD OF THE INVENTION

This invention is directed to an improved system for supplying pressurized air for dental purposes. It is more specifically directed to the novel use of an oil cooled air compressor to efficiently provide a source of pressurized air for use in dental operations.

BACKGROUND OF THE INVENTION

For years dentists have been using standardized utilities, including electricity, pressurized water and air in the dental operations for maintaining, cleaning, repairing and operating on patients' teeth. These utilities are provided to power and operate the various tools which are required in a very efficient and comprehensive way. Thus, without the various utilities to drive and power these tools, the work of a dentist would be very difficult and, in turn, very agonizing to the patient.

One of the necessary utilities that is utilized by dentists, both in the past and present is high pressure air. High pressure air is used to clean areas around the teeth or gums after the drilling and preparation work has been accomplished. In addition, high pressure air is used in an aspirator for providing suction to remove excess saliva and liquid from the patient's mouth. A third use for high pressure air is to drive the dentist's drill which is so important to his work. Although there are other types of drills available, the air driven drill is quite useful in that an air turbine driven by high pressure air drives the drill collet and the drill piece at extremely high rotational speeds. This provides a very effective drilling operation when working on the teeth, while at the same time, providing cooling for the drill piece as well as the internal rotating components of the drill body.

In addition to the above described utilities it has been found desirable to provide a completely portable dental delivery system which can be easily transported from one location to another so that dental work can be performed on handicapped or paralyzed patients as well as shut-in patients caused by age or infirmity. In addition, there is a need for a portable dental unit of this nature which can be utilized in hospitals and convalescent homes. In order to provide a suitable portable dental unit it is necessary to provide a source of clean high pressure air which is required for operating many of the dentist's tools.

In a unit of this nature it is also desirable, if not mandatory, that the unit be extremely quiet because of the nature of the areas in which it will be used. Thus, it is highly desirable to provide a source of pressurized air wherein the compressor unit and system are completely self- contained, extremely quiet and have sufficiently high flow capacity to adequately perform all of the functions required.

None of the prior art devices which are known in the market place are capable of performing this function. In fact, there is no known completely portable dental unit that is presently available. As a result, the applicant's invention has made a completely portable dental unit not only feasible, but practical.

INFORMATION DISCLOSURE STATEMENT

The following patents which are listed and described are believed to be the most pertinent patents to this invention which are known by the inventors. This list is provided in order to comply with the inventors' duty to disclose to the Patent Office any and all information which is material to the examination of this application.

The Mitch patent (U.S. Pat. No. 4,091,638) discloses the internal cooling of a hermetically sealed rotary refrigeration compressor. The compressor is provided with a means for handling the oil and refrigerant vapor mixture to provide sufficient cooling of the motor without external precoolers and related conduits and apparatus. The oil is collected and directed so that the flow is along the internal surface of the hermetic shell so that the shell itself functions as a heat exchanger.

The Stofen patent (U.S. Pat. No. 4,311,439) discloses an air compressor system wherein the motor and compressor are enclosed within a substantially air-tight cabinet for maintaining quiet operation of the unit. This patent describes the use of circulating air which is routed over the compressor to maintain the temperature at a safe level.

The Pownall patent (U.S. Pat. No. 2,606,430) discloses a multiple stage air compressor system wherein the compressor is run in oil to lubricate the bearings of the compressor as well as cool the unit. A separating device is used in this system for separating the entrained oil from the compressed gas so that the outlet gas is relatively oil-free. This patent does not directly relate to the applicant's invention in that it is a large compressor system and there is no direct correlation with the type of system which is disclosed in this application.

The Schibbye patent (U.S. Pat. No. 3,945,216) also discloses a compressor which utilizes an oil separator to separate oil from the compressed refrigeration gases. The oil that is used in this system has a considerably high viscosity which is used to aid the separation function of the system.

The Yanik patent (U.S. Pat. No. 4,060,340) is presented to show the operation of a compressed air system which utilizes an outlet unloading valve. In this system the outlet pressure is removed or unloaded from the outlet of the compressor when it is stopped. A diversion valve is included to provide for blocking any connection of the compressor inlet with the discharge pressure side of the compressor.

SUMMARY OF THE INVENTION

An object of the present invention is to provide a quiet running, oil free air supply for a dental delivery system. In conjunction with this the applicants have designed a completely portable dental operating unit which utilizes modular construction. The individual components of the unit are individually housed in separate box-like containers or modules with the modules designed to interfit and lock with each other to form a work console arrangement. There can be any number of modules forming the console, but it has been found that three modules have proven to be quite satisfactory.

The reason for providing the dental delivery system in modular form is to make it easier to transport and store when patients are serviced in distant or remote locations. The operating unit when the modules are assembled is arranged so that the bottom or lowermost module has a pair of wheels while the upper unit is provided with a handle so that the dental delivery system can be easily moved, similar to the common "dollie". Thus, the dental delivery system can be used in the dentist's office and then moved out of the office to patients' homes, hospitals or business offices. This is a desirable alternative to the present permanent systems and allows the dentist to go to the patient instead of forcing the patient to travel to the dentist.

The present invention provides an oil-free, quiet running pressurized air supply for the dental delivery system. In order to provide the quiet or noise-free characteristic that is so necessary in work of this nature a hermetically sealed refrigeration compressor has been modified and converted in such a way as to provide the unique and unobvious results which are provided by the system.

The high pressure utility air system which is provided by the present invention includes the hermetically enclosed compressor which contains internal collant oil and includes an auxiliary oil cooling and temperature control loop as well as a high pressure air outlet system. Because of the nature of the compressor which is used and the fact that the inlet air passes through the housing of the compressor unit, inlet air as it enters the compressor is entrained with coolant oil vapor which helps to lubricate as well as cool the internal components of the compressor. Because of the use the coolant oil in this way the outlet pressurized air contains a relatively high concentration of oil vapor which is carried with the air as it leaves the compressor unit. This air is passed through an oil coalescer or filter which filters out any contamination or particles as well as condenses the oil to collect the oil in the bottom of the coalescer. Thus, as air leaves the coalescer, it is substantially contamination and oil free. At this point, the air passes through a check-valve and a quick disconnect so that the outlet air from the compressor can be connected to other modules in the delivery system where it is stored in a suitable pressure tank or reservoir. The storage tank, in turn, is connected to a manifold for distribution to the necessary dental tools and accessories.

It is extremely important to maintain the temperature of the motor and compressor within the compressor unit at a safe operating temperature so that the unit can be used for continued or intermittent use. In order to accomplish this, the applicants have provided a unique circulating system whereby the oil is drawn off of the lower portion of the housing of the compressor by a suitable motor-driven pump with the oil forced through an air cooled radiator with the cooled oil directed back into the housing of the motor compressor unit. Since the control of the temperature of the compressor is critical to the satisfactory operation of this unit, the return oil entering the compressor housing is arranged to impinge directly on the top portion of the compressor cylinder head. Since this is the area of highest temperature, it is necessary to control this temperature as well as the other heat generating areas of the unit. With the oil impinging directly on the cylinder head, the oil flows downward across the compressor and motor returning to the reservoir in the lower portion of the housing. In this way, the cooled oil absorbs the generated heat energy from the compressor and motor and maintains the temperature of this unit at a safe operating level.

One of the major problems with a unit of this type is that the coolant oil is entrained in the pressurized air leaving the system. In time, all of the coolant oil would be dissipated and the unit would cease to function. In the present invention, an oil coalscer is provided in the outlet to filter contaminants and separate the oil vapors and droplets from the pressurized air. The coalescer is provided with a normally closed electric solenoid attached to the lowermost portion of the case of the coalescer. It is common practice to unload or depressurize the outlet piping of an air compressor so that pressure is released from the outlet valve of the compressor to reduce the load that is placed on the motor when the compressor is started. In the present invention, a novel arrangement is provided to perform this function wherein the solenoid operates as a pressure unloading valve. The normally closed solenoid remains closed during the operation of the compressor unit and upon the deenergization of the compressor motor the solenoid valve is automatically opened. When the valve is opened the remaining pressure in the air outlet line between the compressor and the outlet check valve is bled off through the coalescer. Since the outlet from the coalescer is in the bottom area, the coolant oil which has accumulated is forced ahead of the pressurized air and through a tube which connects the valve back to the compressor housing. Thus, each time the compressor is deenergized, any accumulated oil is returned to the compressor unit, thereby preventing the loss of the coolant oil and allowing the compressor unit to operate for an extended period of time. This novel arrangement solves many of the problems which have been encountered in the past when an attempt is made to use a hermetically sealed refrigeration compressor unit to pump gases other than refrigerants.

A quiet bladed fan is mounted in conjunction with the oil radiator to provide additional cooling for the radiator during compressor operation. It is possible that this fan can be operated by a thermostat switch sensing the oil temperature within the system, or the fan can run continuously while the dental delivery system is operating. In this way, when the air compressor unit is deenergized, all electrical power is removed from the air system except for the fan which can be arranged to run continuously. This allows additional air flow to be introduced into the compressor module and provide auxiliary cooling within the module.

Other features of this invention will appear in the following description and appended claims, reference being made to the accompanying drawings forming a part of this specification wherein like reference characters designate corresponding parts in the various views.

BRIEF DESCRIPTION OF THE DRAWINGS

FIG. 1 is a perspective view of a modular type portable dental delivery system showing an air pressure storage tank and a portion of an air compressor supply system located in separate modules;

FIG. 2 is a partial sectional view of the air compressor supply system taken along the lines 2—2 of FIG. 1;

FIG. 3 is a partial side elevation view taken along lines 3—3 of FIG. 2 showing the coolant heat exchanger and cooling fan;

FIG. 4 is a partial side elevation view of the air compressor supply system taken along lines 4—4 of FIG. 2;

FIG. 5 is a partial side sectional view showing the air inlet device for the compressor housing; and FIG. 6 is a pictorial schematic showing the coolant and air outlet piping which is part of the dental delivery system according to the present invention.

DETAILED DESCRIPTION OF THE DRAWINGS

Turning now more specifically to the drawings, FIG. 1 shows a dental delivery system 10 composed of boxlike modules or containers 12, 14 and 16. The uppermost module 12 has an extendable front support shelf 18 with dental tools 20 arranged in support bracket 22.

Some of the dental tools 20 are of the air driven type which are connected by flexible lines 24 to an enclosed manifold (not shown) or connecting conduit 26.

A depressed work area or tray 28 can be provided in the uppermost surface of the work module 12. The work area 28 can be protected by a hinged cover 30 and the module can include a hand grip bar 32 provided along the rear edge. A built-in X-ray viewing screen 34 can be mounted in the hinged cover 30. Suitable lighting can be provided within the cover and behind the viewing screen 34 to allow viewing and study of X-ray film.

An intermediate module 14 can include a pressurized air storage tank or reservoir 40 which is connected by flexible tubes 42, 44 having quick-disconnect couplings 46, 48. Previously described conduit 26 can also be arranged in this fashion.

It is desirable to provide quick-disconnect couplings at the interface of each module so that flexible connector tubes 170 can be used to interconnect modules.

The lower module 16 has a forwardly inclined front surface 50. If desired, the front or sides of the individual modules can be hinged so as to provide access within the module. In addition, storage space can be provided within one or more of the modules for storage of various accessories and supplies. A pair of rubber-tired wheels 52, 53 mounted on a suitable shaft 54 is arranged along the lower rear edge of the module 16. An auxiliary set of support wheels 56, 58 are spacedly arranged along the front edge of the module 16 to stabilize the console and hold it in level position. The wheels 56, 58 can include locking means for stabilizing the wheels and prevent them from moving while the console delivery system is in use. In the present arrangement, an air compressor supply system 60 is provided in the lower module 16 for providing clean pressurized air to the storage tank 40 and the dental tools 20.

FIG. 2 shows the air supply system 60 having a suitably mounted refrigeration-type electric motor driven air compressor unit 62. The air compressor unit 62 is mounted through feet 64 to the lower panel 66 of the module 16. The compressor feet 64 are isolated from the panel 66 by suitable vibration dampening material to prevent vibration from being transmitted to the module 16. In this way, the gas compressor unit which is inherently quiet can be further noise dampened to prevent the transfer of vibrations to the module. In this way, the air supply unit is exceedingly quiet and unobtrusive during operation.

The module 16 includes side panels 68, 70 and back panel 72. The wheels 52, 53 are mounted in recessed compartments 74, 76 at the corners of the module.

A 110v AC power receptacle 79 and master switch 78 are mounted on the back panel 72 and are connected through a power indicator light 80 to the gas compressor unit and the other electrical components within the module. A suitable control module and junction box can be provided in the electrical system to properly sequence the operation of the electrically operated components.

The refrigeration type gas compressor unit includes a thin shell outer housing 82 which completely surrounds and encloses the air compressor unit 62. Air inlet openings 84 are provided on the outside of the housing 82 and allow air or gas to pass into the housing 82 and into the suction inlet of the compressor. Air inlet devices 86 are mounted on each of the air inlet tubes 84. A pressurized air outlet fitting 88 is provided on the side of the compressor housing and is internally connected to the outlet of the compressor unit. The air outlet fitting is connected through tube 90 to coalescer 92. A check valve 94 is connected downstream of the air coalescer 92. The check valve 94 is arranged so that pressurized outlet air will flow in the direction of the arrows shown in FIG. 4 and prevents the reverse flow of air back to the compressor. A coupling 96 and tee 98 are connected to the outlet of the check valve 94 with a flexible tube 100 being connected to a quick disconnect coupling 102 mounted on the module rear plate 72. An electrically operated solenoid valve 104 is directly coupled to the bottom portion of the coalescer 92. The outlet of the solenoid valve 104 is connected by flexible tube 106 to a multi-port fitting 134 provided on a return fitting 108 positioned in the upper portion of the housing 82.

The enclosed compressor housing 82 includes a quantity of suitable oil coolant 110 for absorbing heat energy and cooling the internal components within the compressor unit 62. As can be seen in FIG. 4 the oil coolant 110 collects in the lowermost portion of the housing 82. A site guage 112 can be mounted in the side of the housing 82 to reveal the level of the coolant 110 within the housing.

In order to prevent loss of the liquid coolant 110 during operation the coolant which is picked up by the incoming air as it enters the housing provides lubrication for the compressor and is entrained as a vapor in the outlet pressurized air issuing from the compressor unit. Thus, entrained oil vapor passes into the coalescer 92. The coalescer 92 is essentially a filter and includes one or more internal cartridges that filters out any contaminants or particles that might be present in the outlet air and at the same time traps and separates the vaporized oil coolant from the air. The filter cartridges that have been used in the present invention include a separate textile type mesh cartridge having holes in the 3 micron range which is provided for filtering out contaminants. A second cartridge formed from a metal mesh material is provided for separating out the coolant vapor that is carried in the outlet air.

As the coolant is collected 112 in the coalescer it drains to the lowermost portion 114. The outlet connection to the solenoid valve 104 is provided at the lowermost portion of the coalescer housing and in direct communication with the collected coolant 112. As will be explained later, the solenoid valve is energized along with the compressor unit and remains in the closed position during operation. Once the electrical power is removed from the compressor motor the solenoid valve automatically opens allowing the pressure in the outlet portion of the compressor unit which is present within coalescer 92 to be dissipated by being dumped back into the compressor housing 82 through the flexible tube 106. At the time that the solenoid valve 104 is deenergized to the open position the or oil 112 which has accumulated in the reservoir or lower area 114 of the coalescer 92 is forced ahead of the residual air so that the oil is returned through the tube 106 to the housing 82. In this way, the collected oil is not lost, but is returned periodically to the housing each time the compressor unit is shut down. In this way, it is unnecessary to replenish the coolant supply 110 present within the housing 82. In most cases that between 1½ to 2 pints of coolant oil 110 has been found sufficient to provide many hours of continuous system operation.

For automatic operation of the compressor system a pressure regulator switch 120 is connected by tube 122 to one leg of the tee 98. The pressure switch 120 senses the outlet air pressure within the system and automatically controls the electrical circuit to the motor within the compressor unit. The present system has been found to work satisfactorily when the switch is adjusted to operate to maintain the outlet air pressure between 80 to 125 psi.

The compressor auxiliary coolant system includes a conduit loop which circulates and, in turn, cools the liquid coolant 110 to properly maintain the temperature within the compressor housing. A small motor driven hydraulic pump 126 is connected to the housing outlet 124 by means of a tube 128. The pump 126 is arranged to be mounted near the module base 66 so that the pump 126 will be at approximately the same level as the outlet 124. In this way, pump inlet suction problems can be eliminated. The outlet coolant flow from the pump is connected to the inlet 146 of radiator 130 by flexible tube 132.

The outlet 148 of the radiator 130 is connected by tubing 132 to multi-port junction block 134 connected to the fitting 108. The radiator 130 which has proven to be satisfactory is a hair-pin tubular type having tube 140 mounted in mounting blocks 142, 144. The inlet end 146 is attached to tube 132 by means of a suitable clamp. The outlet end 148 is connected in the same manner by means of a clamp to flexible tube 132. Transverse heat conducting fins 150 are spacedly positioned along the tube 140 to conduct heat from the tube 140 in order to dissipate heat energy from the oil by air convection. If desired, as shown in FIG. 3, the radiator 130 can be mounted on the outlet side of a suitable rotating fan 152 which can be mounted over an opening 154 formed in the back module panel 72. Brackets can be arranged to suitably mount the radiator 130 in conjunction with the fan 152. The opening 154 and fan 152 is desirably placed immediately adjacent to the compressor housing 82 so that the residual air flow from the fan 152 will pass through the radiator and directly over the compressor unit 62. In this way, the residual air will serve an additional function by directly cooling the housing 82. The coolant return tube 106 is connected by a means of an elbow 160 to the multiport junction block 134, which in turn, is connected directly to the housing connection 108.

It is important to understand that the housing connection 108 is precisely located in the upper portion of the compressor housing 82 at a point which is precisely located over the compressor cylinder head. In this way, the return coolant which has been reduced in temperature impinges directly upon the cylinder head so that it flows over and downward across the cylinder head and motor carrying heat energy away from the motor compressor unit. It has been found that this closed-loop cooling system is quite satisfactory to maintain the temperature of the compressor unit at a safe operating level. The dispensing of the cooled liquid directly over the compressor has produced new and unique cooling results which could not be anticipated in a compressor unit of this type.

The air supply system 60 as described in this application is quite compact and is very quiet. This is a necessity in a portable dental delivery system. With the individual modules 12, 14 and 16 connected together by suitable fastening means, the console becomes a stable work platform for the dentist. The individual utilities between modules are interconnected by jumper tubes 170, 172 which form a utility interconnect arrangement within the console. This utility interconnect not only accommodates the pressurized air supply, but also electricity and water when required. The electrical master switch for the console 78 can be arranged separately from the incoming and outgoing power receptacle 79 provided on the back panel of the lower module 16. Interconnecting wire cables and receptacles can be arranged on the back panel of the modules. In this way, a totally functional working console is provided to complete the dental delivery system.

FIG. 5 shows the air inlet tubing 84 mounted on the side of the compressor housing 82. An air inlet device 86 having an inlet opening 180, a check-valve 182 and a connecting coupling 184 is mounted on the inlet tubes 84. The ball-type check valve 182 is arranged to remain open when the unit is in the normal vertical position, but will close against the aperture 186 when the air inlet device is tipped beyond a horizontal position. This prevents the coolant oil 110 from running out of the air inlet tube 84 causing loss of the coolant if the module 16 is tipped or upset during storage or transit. It is also possible that a filter median can be inserted into the inlet opening 180 to provide a preliminary filter for the inlet air.

OPERATION

Referring now to FIG. 6 which shows an outline of the air supply system 60, the supply system includes a refrigeration type, hermetically enclosed electric motor driven gas compressor unit. A refrigeration type compressor unit is desirable for this type of use since it is fully enclosed within the housing 82. It has been found that an electric motor driven compressor powered by 110v AC is quite satisfactory for this operation. This also lends itself to the portability factor from the standpoint that most locations have 110v AC power sources readily available. It has been found that a compressor unit having a $\frac{1}{2}$ hp motor and which can deliver compressed gas at a rate of 2.5–3 cfm is quite adequate. In most cases, the outlet air pressure is maintained at a maximum of 125 psi during operation.

The hermetically enclosed refrigeration compressor unit 62 is modified in that the inlet openings 84 are generally left open with the possible addition of an inlet check valve device mounted thereon. Inlet air passes through the compressor housing inlet 84 and flows freely through and around the inside of the housing 82. Most refrigeration type gas compressor units have a propeller or some means of throwing or splashing liquid coolant throughout the interior of the housing. This splash system normally provides cooling of the motor and compressor.

In the present system, in order to supplement and maintain operation of the motor compressor unit at a reasonable temperature level a closed-loop coolant system 190 is provided. The liquid coolant used in the present system is approximately $1\frac{1}{2}$–2 pints of synthetic oil designated as DSL 68, non-detergent, having an API viscosity weight of approximately 30. This oil is presently sold by the Blackhawk Oil Company of Denver, Colo. A coolant oil outlet fitting 88 is provided at the lowermost region of the compressor housing 82 so as to communicate with accumulated oil present in the bottom of the housing. Flexible tube 128 is connected to a suitable electrically motor driven pump 126 through tube 132, heat exchange oil cooler 130, and multi-port connector 134 attached to housing return connector 108. The pump 126 is driven by a 110v AC motor which normally draws a maximum of 2 amperes. This pump is capable of flow rates of approximately 2 gallons per hour (gph). The oil coolant heat exchanger 130 can be a ⅜" tube-type radiator which is manufactured by Dragmaster Manufacturing Company. This radiator is arranged as a double-pass radiator having externally mounted transverse fins for dissipating heat energy and cooling the oil passing therethrough. The housing connector 108 returns the cooled oil from tube 133 directly into the housing 82 so that the cooled oil impinges directly on the cylinder head of the compressor unit 62. The pressurized outlet air issuing from the fitting 88, passes through tube 90, oil coalescer or filter 92, check valve 94 and flexible hose 100 to outlet quick-disconnect coupling 102. An air pressure regulator switch 120 is attached to the air pressure outlet tube 100 through tube 122. The pressure regulator switch is electrically connected to a motor control device which electrically energizes and deenergizes the compressor motor and other electrical components. The coolant oil is picked up by the air passing through the compressor housing 82 and compressed along with the air in the compressor so that oil vapor is entrained in the pressured outlet air issuing from the compressor. This air passes through the oil coalescer or filter 92 which includes filter cartridges which filter out contaminants and particles as well as the oil vapor. The oil vapor is collected within the coalescer 92 so that it accumulates in the lower portion or reservoir part of the coalescer. An electrically operated solenoid valve is connected to the bottom portion of the coalescer and is connected by flexible tube 106 back to the oil return multiport 134. The quick-disconnect coupling 102 serves as an additional check valve, but also allows a jumper hose or tube to be connected to the air supply system so that it can be connected to an air pressure storage tank or vessel which can be located in a separate module.

When 110v AC current is placed on the motor control, the outlet air pressure is sensed by the pressure regulator switch 120 to determine if the outlet pressure in the system is between the desired 80 to 125 psi. If the pressure is lower than 80 psi, the pressure switch closes, energizing the compressor motor and the solenoid valve 104. By energizing the solenoid valve simultaneously with the compressor motor the solenoid valve is moved to the closed position. At the same time a motor on the air fan 152 is energized which causes an air flow of approximately 70 cfm to pass over the oil cooler heat exchanger 130. Residual air after passing through the heat exchanger also is directed over the motor compressor unit and the housing 82 to further cool the housing. Simultaneously with the energization of the compressor motor the oil pump is also started causing the coolant oil to be circulated through the closed loop system 190 circulating the coolant oil at a lower temperature to the housing 82 and directly onto the compressor cylinder head. At the same time, the pressurized air containing coolant oil vapor is discharged from the compressor and through the coalescer 92. The accumulated oil that is removed from the pressurized air sets in the lower portion of the coalescer adjacent to the closed solenoid valve.

When the outlet air pressure reaches the maximum setting of the air pressure regulator switch 120 the switch is opened removing power from the compressor motor, solenoid valve and oil pump. In the present unit the switch is set at a maximum of 125 psi. When the solenoid valve is deenergized, it moves automatically to the open position allowing the residual air pressure in the coalescer and outlet tube 90 to bleed through the solenoid valve and tube 106 to the housing 82. Oil accumulated in the bottom of the coalescer 92 is moved through the tube 106 ahead of the pressurized air. The released oil and air unloads the outlet valve on the compressor so that the motor when it starts will not be overloaded in trying to start the compressor against a high outlet pressure.

While a new and novel dental delivery system has been shown and described in detail in this application, it is to be understood that this invention is not to be considered to be limited to the exact form disclosed. Changes in the detail and construction of this apparatus may be made without departing from the spirit of the invention.

What is claimed is:

1. A quiet, high capacity, pressurized clean air system for a portable dental delivery system, said portable dental delivery system having a plurality of modules which can be joined together in a stacked arrangement forming a work console, said console including air powered tools and accessories for use by a dentist, said pressurized system being built into one of said modules and connected so as to power said tools and accessories, said air system comprising:

(a) a modified hermetically enclosed refrigeration-type compressor unit having a power driven gas compressor, said compressor unit being totally enclosed within a single thin shell housing means, said housing means containing a predetermined quantity of a suitable liquid coolant for absorbing heat energy and maintaining the temperature of said compressor unit during operation;

(b) an external cooling loop means attached to said housing means, said loop means including conduit means having an inlet end attached to a lower portion of said housing means and a return end attached to the upper portion of said housing means, said loop means further including a pump means attached to said conduit means near said inlet end for circulating the liquid coolant from the lower to the upper portion of the housing means, the return end of the conduit means being attached at a precise predetermined location on said housing means so that the returning liquid coolant impinges directly upon the top portion of the gas compressor whereby the coolant will absorb heat energy from the compressor unit and maintain the temperature within the housing means at a suitable operating level;

(c) said housing means having an air inlet and outlet means connected to said compressor unit, the air outlet means being connected to an oil coalescer means and a check valve means to prevent pressurized air from moving toward the compressor unit, said check valve means being arranged downstream of said coalescer means with the outlet means being terminated by a coupling means for quick coupling the air outlet means to a pressure storage tank; and (d) said coalescer means including means for separating liquid coolant from the pressurized outlet air and collecting said coolant in a reservoir area, valve means connected to the coalescer means in communication with said reservoir area, said valve means being closed during operation of the air supply system and opened upon shut-down of the compressor unit to unload air pressure from the outlet means and in turn force the collected coolant through a second conduit means connected between said valve means and the return end of said conduit means attached to the upper portion of said housing means.

2. An air supply system as defined in claim 1 wherein the gas compressor is driven by an electric motor which is close-coupled and positioned within said housing means.

3. An air supply system as defined in claim 1 wherein the liquid coolant is a suitable oil having a sufficient energy absorbtion characteristic to perform the cooling function.

4. An air supply system as defined in claim 1 said oil is a synthetic oil having an API viscosity rating of approximately 30.

5. An air supply system as defined in claim 1 wherein said loop means further includes a heat exchanger means connected in series with said conduit means whereby the temperature of said coolant will be further reduced prior to be returned to the housing means.

6. An air system as defined in claim 1 wherein said heat exchanger means is a fin-type tubular radiator for dissipating energy from said liquid coolant.

7. An air supply system as defined in claim 6 wherein said radiator is mounted downstream of an electrically driven fan to further improve the heat energy dissipation from said coolant.

8. An air supply system as defined in claim 1 wherein air inlet for said housing means is connected to a check valve means to prevent the coolant means within the housing from being dissipated while said portable dental delivery system is being transported.

9. An air supply system as defined in claim 1 wherein said coalescer means includes a filter means for filtering out contamination and separating liquid coolant from the outlet pressurized air.

10. An air supply system as defined in claim 9 wherein said filter means includes a close-mesh filter cartridge and a wire-mesh cartridge, said filter cartridge being arranged to collect contaminants and particles while the wire-mesh cartridge causes entrained coolant to collect so that it can be collected in the reservoir area of the coalescer means.

11. An air supply system as defined in claim 1 wherein said valve means is an electrically operated solenoid valve which is energized to the closed position when the gas compressor is energized.

12. An accoustically dampened pressurized air supply system, said air system comprising:
(a) a modified hermetically enclosed electric motor driven gas compressor unit, said gas compressor unit being totally enclosed within a single thin shell housing means, suitable liquid coolant being provided within said housing for absorbing and conducting heat energy from said compressor unit to maintain the temperature within the housing at a suitable temperature during operation;
(b) an external cooling loop means attached to said compressor housing, said loop means including conduit means having a first end attached at a point near the lower portion of the compressor unit housing means and a return end attached to the upper portion of said housing means, said loop means having a pump means connected in series with said conduit means and positioned near said first end for circulating the liquid coolant from the lower to the upper portion of the housing means, the return end of the conduit means being attached at a predetermined location on said housing means so that the return coolant will impinge directly upon the gas compressor so as to regulate and maintain the temperature of the motor and compressor at a safe level.

13. An air supply system as defined in claim 12 wherein said pump means is driven by an electric motor which is energized continuously while the compressor unit is energized.

14. An air supply system as defined in claim 12 wherein said liquid coolant is a synthetic oil having an API viscosity rating of approximately 30.

15. An air supply system as defined in claim 12 wherein said loop means further includes a heat exchanger means arranged in series with the said conduit means for reducing the temperature of the liquid coolant prior to being returned to the upper portion of said housing means.

16. An air supply system as defined in claim 15 wherein the heat exchanger means is tubular radiator having cooling fins for increasing the efficiency of the heat energy dissipation from said liquid coolant.

17. An air supply system as defined in claim 12 which further includes an air inlet and pressurized air outlet means on said housing means, said pressurized air outlet means being connected in series with a coolant coalescer means, a check valve to prevent the air from reversing flow direction and a quickdisconnect coupling means, said coalescer means including filter cartridge means to remove contaminants from the pressurized outlet air and entrained vaporized coolant, said coolant being collected within a lower portion of said coalescer means and a solenoid energized valve means being attached to said coalescer means at a point adjacent to said collected coolant, said solenoid valve means being retained in a closed position while said compressor unit is energized and switched to the open position when said compressor unit is deenergized so that the pressure remaining in said air outlet means is dissipated by forcing the collected coolant from said coalescer means through a tube connected to said housing to return collected coolant to said housing means each time that the compressor unit is deenergized.

* * * * *